United States Patent [19]

Shou

[11] Patent Number: 5,392,465
[45] Date of Patent: Feb. 28, 1995

[54] MASK FOR USE IN FIRE ACCIDENTS

[76] Inventor: Lee W. Shou, P.O. Box 82-144, Taipei, Taiwan, Prov. of China

[21] Appl. No.: 91,375

[22] Filed: Jul. 15, 1993

[51] Int. Cl.⁶ ............................................. A42B 1/00
[52] U.S. Cl. ................................................... 2/7; 2/9
[58] Field of Search ................... 2/7, 8, 9, 5, 202, 81, 2/205, 173; 128/201.22, 201.23, 201.24, 201.25; 428/920, 921

[56] References Cited

U.S. PATENT DOCUMENTS

| | | | |
|---|---|---|---|
| 596,919 | 1/1898 | Steves | 2/5 |
| 3,458,864 | 8/1969 | Austin et al. | 2/5 |
| 3,535,706 | 10/1970 | Aileo | 2/5 |
| 3,878,563 | 4/1975 | Pulju | 2/9 |
| 4,231,118 | 11/1980 | Nakagawa | 2/7 |
| 4,411,023 | 10/1983 | Pinson | 2/7 |
| 4,514,327 | 4/1985 | Rock | 252/607 |
| 4,637,383 | 1/1987 | Lopez | 2/7 |
| 4,870,959 | 10/1989 | Reisman et al. | 2/7 |
| 4,896,650 | 1/1990 | Hait | 126/9 R |
| 4,935,966 | 6/1990 | Hosouchi et al. | 2/202 |
| 5,016,625 | 5/1991 | Hsu et al. | 128/201.25 |
| 5,040,530 | 8/1991 | Bauer et al. | 2/7 |
| 5,113,527 | 5/1992 | Robertson-McKenzie | 2/7 |
| 5,115,804 | 5/1992 | Brookman | 128/201.22 |
| 5,146,636 | 9/1992 | DeLa Pena | 2/8 |
| 5,233,821 | 8/1993 | Weber, Jr. et al. | 2/8 |

Primary Examiner—Clifford D. Crowder
Assistant Examiner—Michael A. Neas
Attorney, Agent, or Firm—Alfred Lei

[57] ABSTRACT

This invention relates to a mask for use in fire accidents and in particular to one including a body portion adapted to cover face of an user and provided with a transparent visor in the front side, the body portion being made of a fire proof cloth in which is received a liquid chemical substance for preventing smoke, an elastic band made of fire proof material and mounted on the upper rear side of the body portion, a left strap mounted on the lower left side of the body portion and provided with a female fastener, a right strap mounted on the lower right side of the body portion and provided with a male fastener adapted to engage the female fastener off, the left strap, and an aluminum-foil bag for receiving the mask, whereby the user will be prevented from inhaling smoke and being choked by the smoke.

1 Claim, 5 Drawing Sheets

MASK FOR USE IN FIRE ACCIDENTS

BACKGROUND OF THE INVENTION

It has been found that the conventional cloth mask simply utilizes a piece of cloth to separate the face of an user from the outside and enables air to flow in the nose of the user through the cloth. However, such cloth mask cannot keep the user from being hurt by the burning smoke in fire accidents.

Therefore, it is an object of the present invention to provide a mask which may obviate and mitigate the above-mentioned drawbacks.

SUMMARY OF THE INVENTION

This invention relates to an improved mask for use in fire accidents.

It is the primary object of the present invention to provide a mask which is especially helpful in fire accidents.

It is another object of the present invention to provide a mask for use in fire accidents which is supported upon the head and will not interfere with or affect the sight of the user.

It is still another object of the present invention to provide a mask for use in fire accidents which is simple in construction and operation.

It is still another object of the present invention to provide a mask for use in fire accidents which may prevent the user from inhaling smoke.

It is a further object of the present invention to provide a mask for use in fire accidents which may prevent the user from being choked by the smoke.

The invention accordingly consists of features of constructions and method, combination of elements, arrangement of parts and steps of the method which will be exemplified in the constructions and method hereinafter disclosed, the scope of the application of which will be indicated in the claim following.

DETAILED DESCRIPTION OF THE PREFERRED EMBODIMENT

Before explaining the present invention in detail, it is to be understood that the invention is not limited in its application to the details of construction and arrangement of parts illustrated in the accompanying drawings, since the invention is capable of other embodiments and of being practiced or carried out in various ways. Also it is to be understood that the phraseology or terminology employed herein is for the purpose of description and not of limitation.

Figure 1:
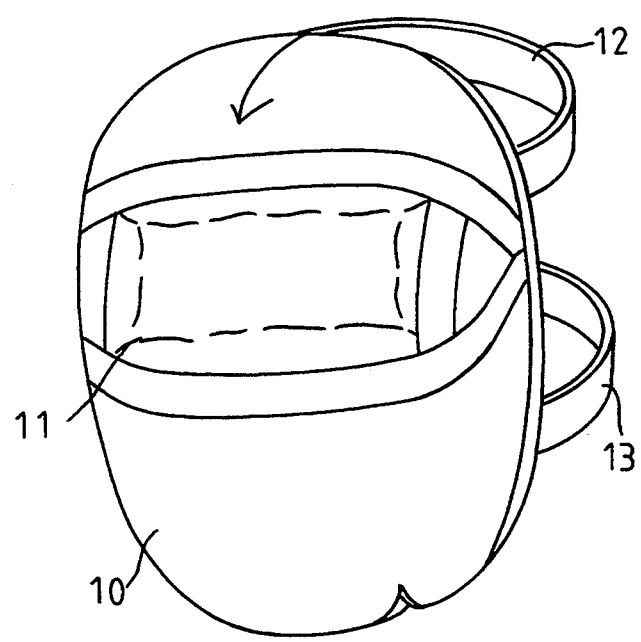
FIG. 1 is a perspective view of a mask according to the present invention.
Figure 2:
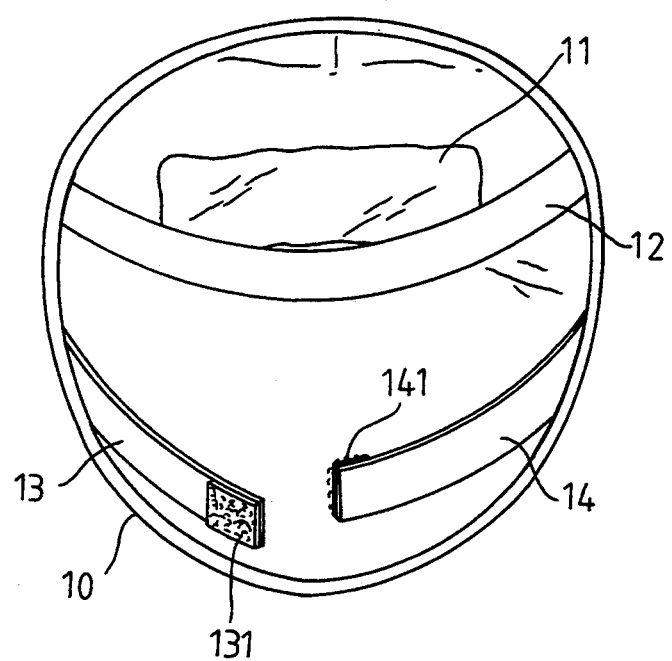
FIG. 2 shows the rear side of the mask.
Figure 3:
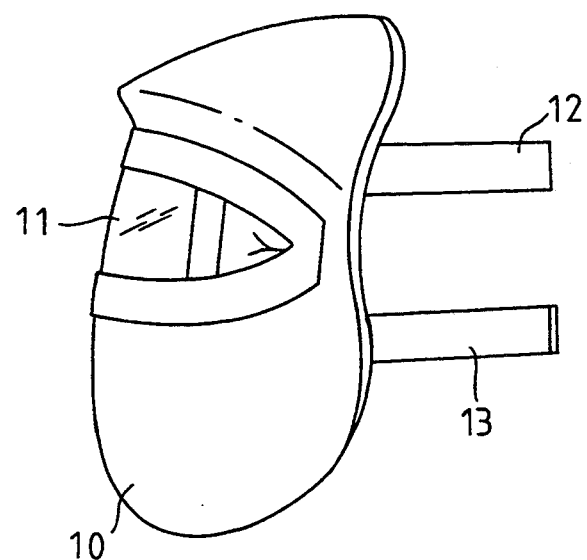
FIG. 3 is a side view of the mask.

With reference to the drawings and in particular to FIGS. 1 and 2 thereof, the mask according to the present invention comprises a body portion 10 adapted to cover the face, mouth and nose of an user. The body portion 10 is formed with a transparent visor 11 in the front side and an elastic band 12 in the rear side. The elastic band 12 is used for firmly keeping the mask on the face of an user and is made of fire proof material. Further, under the elastic band 12, there are a left strap 13 and a right strap 14 which are respectively provided with a female hook and loop fastener 131 and a male hook and loop fastener 141 so that the face of an user can be closely covered with the body portion 10 thereby preventing the eyes, the nose and the face of the user from being hurt.

The body portion 10 is made of any suitable fire proof cloth in which is mounted a layer of cotton and is received a liquid chemical substance for preventing smoke from passing therethrough. The liquid chemical substance is well known in the art and is not considered part of the invention. As shown in FIG. 10, when an user wears the mask, the elastic band 12 is just located at the upper portion of the user's head while the left and the right straps 13 and 14 at the lower portion of the user's head. Hence, the mask can be fixed on the head of the user by engaging the male hook and loop fastener 141 of the right strap 14 with the female hook and loop fastener 131 of the left strap 13.

Figure 4:
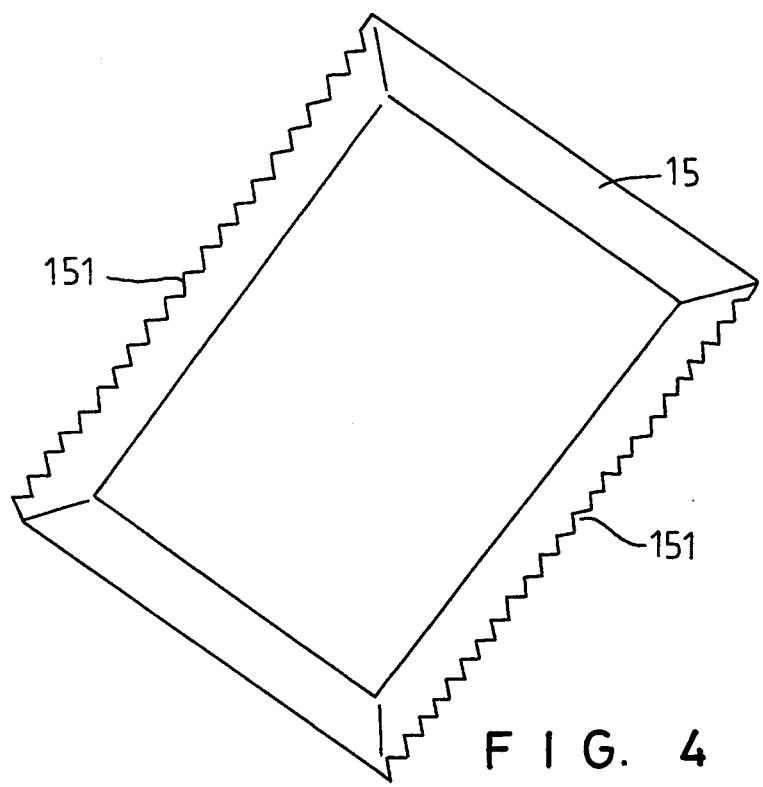
FIG. 4 shows an aluminum-foil bag for receiving the mask.

Looking now at FIG. 4, the mask according to the present invention is normally put in a bag is made of aluminum foil. In order to make it easier to tear open the bag 15, both sides of the bag 15 are provided with a toothed edge 151.

Figure 5:
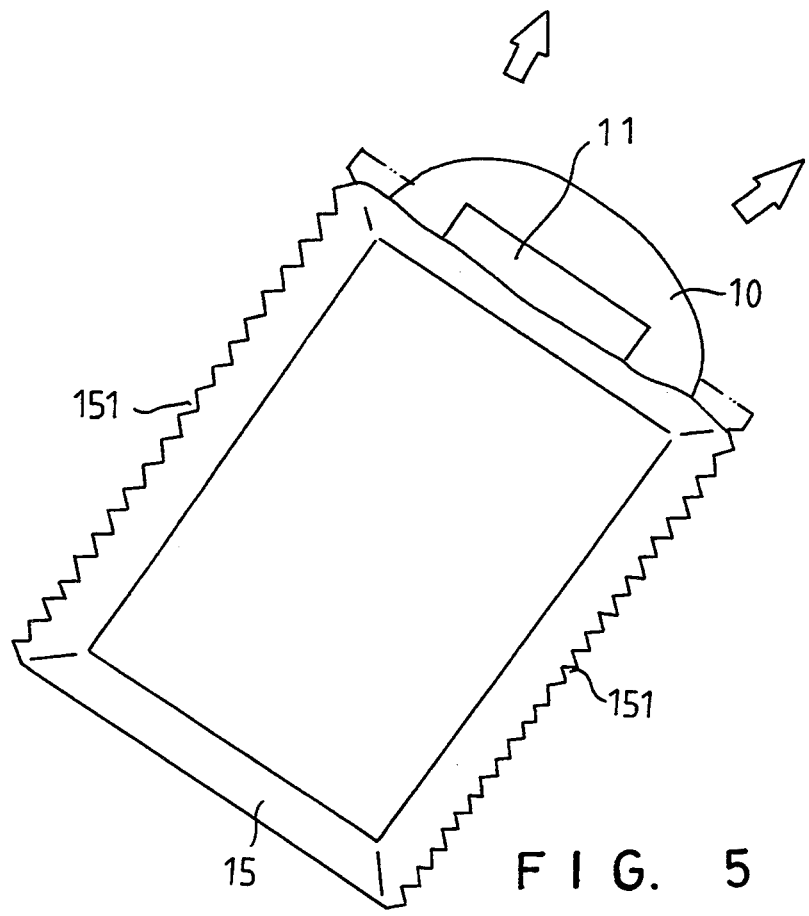
FIG. 5 shows the way to take out the mask from the aluminum-foil bag.
Figure 6:
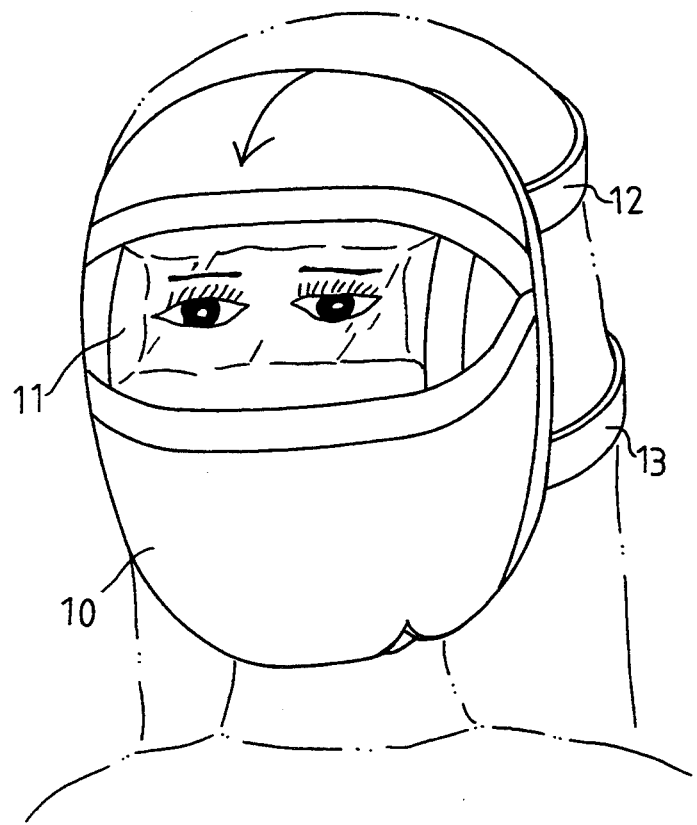
FIG. 6 is a working view of the present invention.

As illustrated in FIG. 5, when in use, simply tear off the bag 15 along a tearing line 15 and take out the mask 11 for use. Then, the mask may be conveniently worn on the head of an user.

The invention is naturally not limited in any sense to the particular features specified in the forgoing or to the details of the particular embodiment which has been chosen in order to illustrate the invention. Consideration can be given to all kinds of variants of the particular embodiment which has been described by way of example and of its constituent elements without thereby departing from the scope of the invention. This invention accordingly includes all the means constituting technical equivalents of the means described as well as their combinations.

I claim:

1. A combination of a mask and a bag for use in fire accidents comprising:

a body portion adapted to cover face of an user and provided with a transparent visor in the front side, said body portion being made of a fire proof cloth in which is received a liquid chemical substance for preventing smoke;

an elastic band made of fire proof material and mounted on an upper rear side of said body portion;

a left strap mounted on a lower left side of said body portion and provided with a female fastener; and a right strap mounted on a lower right side of said body portion and provided with a male fastener adapted to engage the female fastener of said left strap;

said bag being made of aluminum foil and adapted for receiving said mask.

* * * * *